United States Patent
Al-Abdullah et al.

(10) Patent No.: US 11,579,051 B2
(45) Date of Patent: Feb. 14, 2023

(54) STABLE DITHIZONE SOLUTIONS AND FORMULATIONS AND METHODS FOR THEIR USE

(71) Applicant: CITY OF HOPE, Duarte, CA (US)

(72) Inventors: Ismail H. Al-Abdullah, Azusa, CA (US); Meirigeng Qi, Duarte, CA (US); Bashar Khiatah, Duarte, CA (US); Luis Valiente, Burbank, CA (US)

(73) Assignee: CITY OF HOPE, Duarte, CA (US)

( * ) Notice: Subject to any disclaimer, the term of this patent is extended or adjusted under 35 U.S.C. 154(b) by 393 days.

(21) Appl. No.: 16/815,442

(22) Filed: Mar. 11, 2020

(65) Prior Publication Data

US 2020/0319065 A1    Oct. 8, 2020

Related U.S. Application Data (60) Provisional application No. 62/816,802, filed on Mar. 11, 2019.

(51) Int. Cl.
*C07C 337/06* (2006.01)
*G01N 1/30* (2006.01)

(52) U.S. Cl.
CPC .......... *G01N 1/30* (2013.01); *C07C 337/06* (2013.01); *G01N 2001/302* (2013.01)

(58) Field of Classification Search
None
See application file for complete search history.

(56) References Cited

U.S. PATENT DOCUMENTS

2013/0172500 A1* 7/2013 Morrison .............. C08F 210/16
502/154

OTHER PUBLICATIONS

Bader, E., et al., "Identification of Proliferative and Mature β-Cells in the Islets of Langerhans," Nature 535:430-434 (2016).
Bakhti, M., et al., "Modelling the Endocrine Pancreas in Health and Disease," Nat. Rev. Endocrinol. 15:155-171 (2019).
Buchwald, P., et al., "Fully Automated Islet Cell Counter (ICC) for the Assessment of Islet Mass, Purity, and Size Distribution by Digital Image Analysis," Cell Transplant. 25:1747-1761 (2016).
Christudoss, P., et al., "Zinc Status of Patients with Benign Prostatic Hyperplasia and Prostate Carcinoma," Indian J. Urol. 27(1):14-18 (2011).
Clark, S. A., et al., "Staining and In Vitro Toxicity of Dithizone with Canine, Porcine, and Bovine Islets," Cell Transplantation 3(2):299-306 (1994).

(Continued)

*Primary Examiner* — Sudhakar Katakam
*Assistant Examiner* — Jennifer C Sawyer
(74) *Attorney, Agent, or Firm* — Perkins Coie LLP; Lara J. Dueppen (57) ABSTRACT

An optimized Dipheylthiocarbazone or Dithizone (DTZ) solution was developed with preferred physical and chemical properties to characterize human islets and insulin producing cells differentiated from embryonic stem cells. Application of the newly formulated iDTZ (i stands for islet) over a range of temperatures, time intervals and cell and tissue types found to be robust for identifying these cells. The iDTZ, through high transition zinc binding, concentrated in insulin producing cells could also be used to delineate zinc levels in tissue and liquid samples.

19 Claims, 8 Drawing Sheets
(7 of 8 Drawing Sheet(s) Filed in Color)

(56) References Cited

OTHER PUBLICATIONS

Easley, C. J., et al., "Quantitative Measurement of Zinc Secretion from Pancreatic Islets with High Temporal Resolution Using Droplet-Based Microfluidics," Anal. Chem. 81(21):9086-9095 (2009).
Ellis, C., et al., "Regenerative Medicine and Cell-Based Approaches to Restore Pancreatic Function," Nat. Rev. Gastroenterol. Hepatol. 14:612-628 (2017).
Friberg, A. S., et al., "Quantification of the Islet Product: Presentation of a Standardized Current Good Manufacturing Practices Compliant System with Minimal Variability," Transplantation 91:677-683 (2011).
Furuyama, K., et al., "Diabetes Relief in Mice by Glucose-Sensing Insulin-Secreting Human α-Cells," Nature 567(7746):43-48 (2019).
Hering, B. J., et al., "Phase 3 Trial of Transplantation of Human Islets in Type 1 Diabetes Complicated by Severe Hypoglycemia," Diabetes Care 39:1230-1240 (2016).
Jindal, R. M., et al., "A New Method for Quantification of Islets by Measurement of Zinc Content," Diabetes 41:1056-1062 (1992).
Khiatah, B., et al., "Evaluation of Collagenase Gold Plus BP Protease in Isolating Islets from Human Pancreata," Islets 10(2):51-59 (2018).
Kissler, H. J., et al., "Validation of Methodologies for Quantifying Isolated Human Islets: An Islet Cell Resources Study," Clin. Transplant. 24(2):236-242 (2010).
Kracht, M. J.L., et al., "Autoimmunity Against a Defective Ribosomal Insulin Gene Product in Type 1 Diabetes," Nat. Med. 23(4):501-507 (2017).
Latif, Z. A., et al., "A Simple Method of Staining Fresh and Cultured Islets," Transplantation 45:827-830 (1988).
Li, D., et al., "Imaging Dynamic Insulin Release Using a Fluorescent Zinc Indicator for Monitoring Induced Exocytotic Release (ZIMIR)," PNAS 108(52):21063-21068 (2011).
McNary, Jr., W. F., "Zinc-Dithizone Reaction of Pancreatic Islets," J. Histochem. Cytochem. 2:185-195 (1954).
Nair, G. G., et al., "Recapitulating Endocrine Cell Clustering in Culture Promotes Maturation of Human Stem-Cell-Derived β-Cells," Nat. Cell. Biol. 21(2):263-274 (2019).
O'Hallorah, T. V., et al., "Zinc, Insulin, and the Liver: A Menage a Trois," J. Clin. Invest. 123(10):4136-4139 (2013).
Qi, M., et al., "Human Pancreatic Islets Isolated from Donors with Elevated HbA1c Levels: Islet Yield and Graft Efficacy," Cell Transplant. 24:1879-1886 (2015).
Qian, W.J., et al., "Imaging of $Zn^{2+}$ Release from Pancreatic β-Cells at the Level of Single Exocytotic Events," Anal. Chem. 75:3468-3475 (2003).
Rezania, A., et al., "Reversal of Diabetes with Insulin-Producing Cells Derived In Vitro from Human Pluripotent Stem Cells," Nat. Biotechnol. 32(11):1121-1133 (2014).
Ricordi, C., et al., "National Institutes of Health-Sponsored Clinical Islet Transplantation Consortium Phase 3 Trial: Manufacture of a Complex Cellular Product at Eight Processing Facilities," Diabetes 65:3418-3428 (2016).
Shiroi, A., et al., "Identification of Insulin-Producing Cells Derived from Embryonic Stem Cells by Zinc-Chelating Dithizone," Stem Cells 20:284-292 (2002).
Temiz, M. Z., et al., "The Use of Serum Zinc to Prostate-Specific Antigen Ratio as a Biomarker in the Prediction of Prostate Biopsy Outcomes," Biomark. Med. 13(02):59-68 (2019).
Tian, X., et al., $Zn^{II}$ Complexes for Bioimaging and Correlated Applications, Chem. Asian J. 14:509-526 (2019).
Wang, L-J., et al., "Application of Digital Image Analysis to Determine Pancreatic Islet Mass and Purity in Clinical Islet Isolation and Transplantation," Cell Transplant. 24(7):1195-1204 (2015).
Yuan, D. S., "Dithizone Staining of Intracellular Zinc: An Unexpected and Versatile Counterscreen for Auxotrophic Marker Genes in *Saccharomyces cerevisiae*" PLoS One 6(10):e25830 (2011).
Zhou, Q., et al., "Pancreas Regeneration," Nature 557(7705):351-358 (2018).

\* cited by examiner

STABLE DITHIZONE SOLUTIONS AND FORMULATIONS AND METHODS FOR THEIR USE

PRIORITY CLAIM

This application claims the benefit of U.S. Provisional Patent Application No. 62/816,802, filed Mar. 11, 2019, which is incorporated herein by reference in its entirety, including drawings.

BACKGROUND

The pancreas is composed of endocrine islets, exocrine acinar and ductal cells. The endocrine islets synthesize and secrete insulin in response to secretagogues to control and regulate glucose homeostasis. The islets consist of α, β, δ, PPP, and € secreting glucagon, insulin, somatostatin, pancreatic polypeptide and ghrelin respectively. The exocrine acinar cells secrete several proteases, lipase and amylase for digestion of the protein, fat and carbohydrate metabolism in the gut (1-4).

Individuals with type 1 diabetes (T1D) experience autoimmune-mediated destruction of insulin producing β-cells and consequently require life-long insulin therapy (5). Pancreatic islet transplantation (IT) is a cellular therapy for treating type 1 diabetes (6). It is currently being evaluated by Food and Drug Administration (FDA) for potentially licensing and standard treatment. The whole procedure of this treatment includes manufacturing human islets from cadaveric donor pancreata, evaluating quality of the final products, and transplanting the islet products into patients with T1D. However, the success of IT is reliant on the quality, purity, and quantity of islets (7). Isolating human islets requires chemically digesting the pancreatic tissue followed by separating the small amount of islets from mass amount of non-islet tissue using a density gradient approach.

To ensure success, rigorous methods for pre-transplant islet evaluation are needed. One such technique employs DTZ, which stains high-zinc containing β-cells red in contrast to unstained acinar and ductal cells types and is a standard approach for islet characterization (8). However, current DTZ formulations when used in solution are highly unstable, must be prepared fresh daily and have essentially no shelf-life. The lack of stability and shelf life hampers reproducibility in the characterization of different cell types, including islet β-cells (9) and yeast (10). Thus, it is desirable to develop formulations to improve stability and shelf-life.

SUMMARY

In certain embodiments, a stable solution of dithizone (DTZ) is provided. The stable DTZ solution comprises a plurality of solutes comprising DTZ, ammonium hydroxide, and a salt mixture; and a solvent comprising a mixture of DMSO, methanol, water, and a buffering agent.

In some embodiments, a stable DTZ formulation is provided, wherein the formulation comprises: a first solution comprising DTZ dissolved in DMSO, methanol, and a solution of ammonium hydroxide; and a second solution comprising a salt mixture dissolved in water and a buffer solution; wherein the first and second solution are combined to form a final DTZ solution.

In certain embodiments, a method for preparing a stable solution of DTZ is provided, the method comprising: (i) preparing a first solution comprising the following steps: dissolving a quantity of DTZ in DMSO; adding a solution of methanol to the DTZ dissolved in DMSO; adding a solution of ammonium hydroxide to the DTZ dissolved in DMSO and methanol; and stirring the solution of DTZ under alkaline conditions until the DTZ solution does not contain particles; (ii) preparing a second solution comprising the following steps: combining a salt mixture with HEPES buffer solution; adding deionized and double distilled water to the salt mixture and HEPES buffer; adjusting the pH of the salt buffer solution to approximately 7.2; and combining the second solution with the first solution to form the final stable solution of DTZ.

In some embodiments, the concentration of DTZ in the final stable solution or formulation is approximately 1.6 g/L. In some embodiments, the molar concentration of ammonium hydroxide in the final stable solution or formulation is approximately 1M.

In some embodiments, the salt mixture of the final stable solution or formulation comprises a Zinc absorbing agent such as sodium D-gluconate. In some embodiments, the salt mixture comprises Sodium chloride (NaCl), sodium D-gluconate (D-Nagluconate), sodium acetate trihydrate (NaAc•3H$_2$O), potassium chloride (KCl), calcium chloride dihydrate (CaCl$_2$•2H$_2$O), and magnesium chloride hexahydrate (MgCl$_2$·6H$_2$O). And in some embodiments, the concentration of NaCl in the final stable solution or formulation is between approximately 2 to 2.1 g/L; the concentration of D-Nagluconate is between approximately 2 to 2.1 g/L; the concentration of KCl is between approximately 2 to 2.1 g/L; the concentration of NaAc•3H$_2$O is between approximately 2.7 to 2.8 g/L; the concentration of CaCl$_2$•2H$_2$O is between approximately 0.15-0.25 g/L; and the concentration of MgCl$_2$•6H$_2$O is between approximately 0.1 to 0.2 g/L.

In some embodiments, the volume of solvent in the final stable solution or formulation is approximately 20% DMSO and approximately 12% methanol. In certain embodiments, the buffering agent in the final stable solution or formulation is a 1M HEPES solution.

BRIEF DESCRIPTION OF THE DRAWINGS

This application contains at least one drawing executed in color. Copies of this application with color drawing(s) will be provided by the Office upon request and payment of the necessary fees.

FIGS. 2A-2C show that solutions of iDTZ have improved islet staining under various conditions employing an automated quantification system.

FIGS. 3A-3C show that human islets and insulin producing cells differentiated from embryonic stem cells are rapidly identified by iDTZ.

DETAILED DESCRIPTION

Stabilized dithizone (DTZ) solutions and methods for using the same are provided herein. Dithizone (DTZ) is zinc-chelating dye and has been used for staining pancreatic islet that contains zinc-enriched islet β- and α-cells. Therefore, this dye has been widely used during islet isolation process to differentiate human islets from non-islet tissue such as exocrine and ductal cells. DTZ has been used to evaluate the purity, quantity, as well as quality of the islets for both transplant and research application. DTZ has also been used to stain insulin-producing cells induced from stem cells.

For staining islets, the current DTZ solution has to be prepared freshly on the day of use. It is prepared by dissolving DTZ dye powder in 20% DMSO and DPBS then filtered with 0.2 μm filter. Although this method can identify the islets, the DTZ solution is not stable and can only be used within one hour of preparation unless it is filtered again which provide inconsistent results especially for islet counting. Therefore lot-to-lot variability has been a major problem. Furthermore, because of the toxicity of the DMSO, it can only be used for limited amount of representative islet samples. Additionally, the islets tend to be stained ineffectually after culture, which limits the study using cultured islets. A proprietary method and formulation for a stable iDTZ solution that addresses the shortcomings of the standard DTZ solution is described herein.

Stable iDTZ Solution

According to some embodiments, a stable solution of islet dithizone (iDTZ) includes a mixture of DTZ and other solutes in a mixture of solvents including DMSO, methanol, water, and a buffer. While standard DTZ solutions only include DTZ alone in solution (of DMSO and DPBS), stable iDTZ includes other solutes including, but not limited to, ammonium hydroxide, and a salt mixture. In some embodiments, the concentration of DTZ in the stable iDTZ solution is comparable to the concentration of DTZ in the standard DTZ solution. For example, in one embodiment, the concentration of DTZ in the stable iDTZ solution is approximately 1.6 g/L.

In certain embodiments, the ammonium hydroxide is added to the stable iDTZ solution as a pre-mixed solution prepared or obtained in advance of preparing the stable iDTZ solution. For example, a solution of ammonium hydroxide of any concentration may be purchased commercially or may be prepared from scratch. That solution may be diluted prior to being added to the iDTZ solution or may be prepared at a concentration that is added to the iDTZ solution without dilution. In one embodiment, the molar concentration of the ammonium hydroxide in the final volume of iDTZ solution is 1 M.

In some embodiments, the salt mixture includes a Zinc absorbing agent such as sodium D-gluconate (D-Nagluconate). In certain embodiments, the salt mixture includes suitable salts including, but not limited to, sodium chloride (NaCl), sodium D-gluconate (D-Nagluconate), sodium acetate trihydrate (NaAc•3H2O), potassium chloride (KCl), calcium chloride dihydrate ($CaCl_2$•2H2O), and magnesium chloride hexahydrate (MgCl2•6H2O). In the final stable iDTZ solution The amount of each salt present in the stable iDTZ solution may be tailored to a final predetermined volume or concentration. In one embodiment, the concentration of NaCl present in the iDTZ solution is between approximately 2 to 2.1 g/L. In one embodiment, the concentration of D-Nagluconate in the iDTZ solution is between approximately 2 to 2.1 g/L. In one embodiment, the concentration of KCl in the iDTZ solution is between approximately 2 to 2.1 g/L. In one embodiment, the concentration of NaAc•3H2O in the iDTZ solution is between approximately 2.7 to 2.8 g/L. In one embodiment, the concentration of $CaCl_2$•2H2O in the iDTZ solution is between approximately 0.15-0.25 g/L. In one embodiment, the concentration of $MgCl_2$•6H2O is between approximately 0.1 to 0.2 g/L. In one embodiment, the salt mixture includes the salts at the concentrations shown in Table 1.

TABLE 1

| Salt | Amount |
|---|---|
| Sodium chloride (NaCl) | Approximately 2.016 g/L |
| Sodium D-gluconate (D-Nagluconate) | Approximately 2.016 g/L |
| Sodium acetate trihydrate (NaAc•3H2O) | Approximately 2.7552 g/L |
| Potassium chloride (KCl) | Approximately 0.2016 g/L |
| Calcium chloride dihydrate ($CaCl_2$•2H2O) | Approximately 0.2 g/L |
| Magnesium chloride hexahydrate ($MgCl_2$•6H2O) | Approximately 0.164 g/L |

The stable iDTZ solution is an aqueous mixture of solvents including DMSO, methanol, water, and a buffer. In some embodiments, the aqueous mixture is approximately 20% DMSO. In some embodiments, the aqueous mixture is approximately 12% methanol. stable iDTZ solution.

In certain embodiments, the buffer is a HEPES (4-(2-hydroxyethyl)-1-piperazineethanesulfonic acid) solution. The HEPES solution may be added to the stable iDTZ solution as a pre-mixed solution prepared or obtained in advance of preparing the stable iDTZ solution. For example, a solution of HEPES of any concentration may be purchased commercially or may be prepared from scratch. That solution may be diluted prior to being added to the iDTZ solution or may be prepared at a concentration that is added to the iDTZ solution without dilution. In one embodiment, the molar concentration of the HEPES in the final volume of iDTZ solution is 1 M.

In one embodiment, the stable iDTZ solution includes the components listed in Table 2 below for every liter of the solution.

TABLE 2

| Component | Amount |
|---|---|
| DTZ | Approximately 1.6 g/L |
| NaCl | Approximately 2.016 g/L |
| D-Nagluconate | Approximately 2.016 g/L |
| NaAc•3H2O | Approximately 2.7552 g/L |
| KCl | Approximately 0.2016 g/L |
| $CaCl_2$•2H2O | Approximately 0.2 g/L |
| $MgCl_2$•6H2O | Approximately 0.164 g/L |
| Ammonium hydroxide | Volume to bring molar concentration to Approximately 1M |
| HEPES | Volume to bring molar concentration to Approximately 1M |
| Methanol | 120 mL |
| DMSO | 200 mL |
| Deionized | Volume to bring total solution volume to |

TABLE 2-continued

| Component | Amount |
|---|---|
| and double distilled water | 1 L |

Stable iDTZ Formulation

A stable iDTZ formulation includes two solutions—a first solution and a second solution—each prepared separately. Then, the two solutions are combined to form a final iDTZ solution. According to certain embodiments, the first of the two solutions includes DTZ dissolved in a solution of DMSO, methanol and ammonium hydroxide. While standard DTZ solutions dissolve DTZ alone in a solution of DMSO and DPBS, the stable iDTZ formulation involves additional solutes and solutes. In some embodiments, approximately 1.6 g of DTZ is dissolved in the first solution, where the first and second solutions are formulated to make 1 L of the final iDTZ solution (i.e., 1.6 g per 1 L final iDTZ solution). The volume of the first solution is approximately 328 mL for each liter of final iDTZ solution. The solvents that comprise the first solution include approximately 200 mL of DMSO for each liter of final iDTZ solution and approximately 120 mL of methanol for each liter of final iDTZ solution.

The first iDTZ solution also includes approximately 8 mL of an ammonium hydroxide solution at a concentration of approximately 4.38 g $NH_4OH$/per mL (for each liter of final iDTZ solution), such that the formulation of the final iDTZ solution includes ammonium hydroxide at a molar concentration of approximately 1M. In certain embodiments, the ammonium hydroxide solution is added to the first solution as a pre-mixed solution prepared or obtained in advance of preparing the first solution. For example, a solution of ammonium hydroxide of any concentration may be purchased commercially or may be prepared from scratch. That solution may be diluted prior to being added to the first solution or may be prepared at a concentration that is added to the first solution without dilution.

According to certain embodiments, the second of the two solutions includes a salt mixture dissolved in water and a buffer solution.

In some embodiments, the salt mixture includes a Zinc absorbing agent such as sodium D-gluconate (D-Nagluconate). In certain embodiments, the salt mixture includes suitable salts including, but not limited to, sodium chloride (NaCl), sodium D-gluconate (D-Nagluconate), sodium acetate trihydrate (NaAc•3H2O), potassium chloride (KCl), calcium chloride dihydrate ($CaCl_2$•2H2O), and magnesium chloride hexahydrate ($MgCl_2$•6H2O).

In some embodiments, the amount of NaCl present in second solution is between approximately 2 to 2.1 g. In one embodiment, the amount of D-Nagluconate in the iDTZ solution is between approximately 2 to 2.1 g. In one embodiment, the amount of KCl in the iDTZ solution is between approximately 2 to 2.1 g. In one embodiment, the amount of NaAc•3H2O in the iDTZ solution is between approximately 2.7 to 2.8 g. In one embodiment, the amount of $CaCl_2$•2H2O in the iDTZ solution is between approximately 0.15-0.25 g. In one embodiment, the amount of $MgCl_2$•6H2O is between approximately 0.1 to 0.2 g. The amount of each salt dissolved in the second solution may be tailored to a predetermined volume of the final iDTZ solution. For example, the amount of each salt dissolved in the second solution is tailored to each liter of final iDTZ solution.

The volume of the second solution is approximately 672 mL for each liter of final iDTZ solution. The solvents that comprise the second solution include approximately 16.8 mL of a HEPES buffer solution at a concentration of approximately 14.1845952 g HEPES per mL (for each liter of final iDTZ solution), such that the formulation of the final iDTZ solution includes HEPES at a molar concentration of approximately 1M. The HEPES solution may be added to the second solution as a pre-mixed solution prepared or obtained in advance of preparing the second solution. For example, a solution of HEPES of any concentration may be purchased commercially or may be prepared from scratch. That solution may be diluted prior to being added to the second solution or may be prepared at a concentration that is added to the second solution without dilution. The remainder of the approximately 672 mL solution is water (e.g., deionized and double distilled water).

In one embodiment, the stable iDTZ formulation includes first and second solutions including the components listed in Table 3 below for every liter of final iDTZ Solution

TABLE 3

| Solution | Components | Amount |
|---|---|---|
| First Solution (S1) | DTZ | Approximately 1.6 g |
| | DMSO | Approximately 200 mL |
| | Methanol | Approximately 120 mL |
| | Ammonium Hydroxide | Approximately 8 mL (approximately 4.38 g/mL) |
| | | TOTAL VOL: 328 mL |
| Second Solution (S2) | NaCl | Approximately 2.016 g |
| | D-Nagluconate | Approximately 2.016 g |
| | NaAc•3H2O | Approximately 2.7552 g |
| | KCl | Approximately 0.2016 g |
| | $CaCl_2$•2H2O | Approximately 0.2 g |
| | $MgCl_2$•6H2O | Approximately 0.164 g |
| | HEPES | Approximately 16.8 mL (approximately 14.1845952 g/L) |
| | Deionized and double distilled water | Volume to bring total solution volume to 672 mL |
| | | TOTAL VOL: 672 mL |
| Final iDTZ Solution | S1 + S2 | TOTAL VOL: 1000 mL |

Methods for Preparing a Stable iDTZ Solution

According to the embodiments described herein, the iDTZ solutions and formulations described above may be prepared using the methods described below. In certain embodiments, the method for preparing a stable solution of dithizone (DTZ) includes a step of preparing a first solution, a step of preparing a second solution, and a step of combining the second solution with the first solution, thereby resulting in the final stable solution of DTZ (i.e., the final iDTZ solution). The first and second solution may be prepared in any order. According to the embodiments described above, the first solution, the second solution, and the final iDTZ solution may be a formulation or solution in accordance with the solutions and formulations described above.

Preparing the First Solution

In some embodiments, the first solution is prepared by dissolving a quantity of DTZ in a volume of DMSO by stirring. In some embodiments, the quantity of DTZ is approximately 1.6 g and the volume of DMSO is approximately 200 mL.

Continuing to stir the solution, a solution of methanol is added to the DTZ dissolved in DMSO. In some embodiments, the volume of methanol is approximately 120 mL.

Continuing to stir the solution, a solution of ammonium hydroxide is added to the DTZ dissolved in DMSO and methanol. In some embodiments, the volume of ammonium hydroxide solution added to the first solution is approximately 8 mL at a concentration of approximately 4.38 g $NH_4OH$/per mL (for each liter of final iDTZ solution), such that the formulation of the final iDTZ solution includes ammonium hydroxide at a molar concentration of approximately 1M. In certain embodiments, the ammonium hydroxide solution is added to the first solution as a pre-mixed solution prepared or obtained in advance of preparing the first solution. For example, a solution of ammonium hydroxide of any concentration may be purchased commercially or may be prepared from scratch. That solution may be diluted prior to being added to the first solution or may be prepared at a concentration that is added to the first solution without dilution.

The first solution is stirred continuously to completely dissolve the DTZ until the first solution does not contain any particles. In some embodiments, the first solution may be stirred under alkaline conditions, and the pH may by approximately 10.12.

Preparing the Second Solution

In some embodiments, the second solution is a salt buffer solution prepared by dissolving a salt mixture with a buffer solution (e.g., a HEPES buffer solution) and water (e.g., deionized and double distilled water). In some embodiments, the salt mixture includes a Zinc absorbing agent such as sodium D-gluconate (D-Nagluconate). In certain embodiments, the salt mixture includes suitable salts including, but not limited to, sodium chloride (NaCl), sodium D-gluconate (D-Nagluconate), sodium acetate trihydrate (NaAc•3H2O), potassium chloride (KCl), calcium chloride dihydrate ($CaCl_2$•2H2O), and magnesium chloride hexahydrate ($MgCl_2$•6H2O). In some embodiments, the amount of NaCl present in second solution is between approximately 2 to 2.1 g. In one embodiment, the amount of D-Nagluconate in the iDTZ solution is between approximately 2 to 2.1 g. In one embodiment, the amount of KCl in the iDTZ solution is between approximately 2 to 2.1 g. In one embodiment, the amount of NaAc•3H2O in the iDTZ solution is between approximately 2.7 to 2.8 g. In one embodiment, the amount of $CaCl_2$•2H2O in the iDTZ solution is between approximately 0.15-0.25 g. In one embodiment, the amount of $MgCl_2$•6H2O is between approximately 0.1 to 0.2 g.

The volume of the second solution is approximately 672 mL. In one embodiment, the volume of the second solution is approximately 16.8 mL of a HEPES buffer solution at a concentration of approximately 14.1845952 g/mL, such that the formulation of the final iDTZ solution includes HEPES at a molar concentration of approximately 1M. The HEPES solution may be added to the second solution as a pre-mixed solution prepared or obtained in advance of preparing the second solution. For example, a solution of HEPES of any concentration may be purchased commercially or may be prepared from scratch. That solution may be diluted prior to being added to the second solution or may be prepared at a concentration that is added to the second solution without dilution. The remainder of the approximately 672 mL solution is water (e.g., deionized and double distilled water).

In some embodiments, the pH of the salt buffer solution is adjusted to approximately 7.2.

Preparing the Final iDTZ Solution

According to the embodiments described herein, the method for preparing the final stable iDTZ solution includes a step of combining the first and second solutions prepared as discussed above to generate a final stable iDTZ solution of approximately 1 L. The first and second solutions are added together slowly with continuous stirring such that no particles or precipitation should form. As a result, no filtering is needed, but is optional. The pH of the final solution should be approximately 7.2.

In some embodiments, the final solution may be divided and packed into multiple containers for storage or for sale, e.g., containers having a volume of 50 mL, 100 mL, 150 mL, 200 mL, 250 mL, 300 mL, 350 mL, 400 mL, 450 mL, 500 mL, 550 mL, 600 mL, 650 mL, 700 mL, 750 mL, 800 mL, 850 mL, 900 mL, 950 mL, or 1 L.

While the method described above is formulated for each liter of final iDTZ solution desired, the final volume may be proportionally scaled up or down accordingly.

Preliminary studies show that the stable iDTZ formulation has the following advantages over standard DTZ solution: (i) the method stabilizes the solution and can be stored indefinitely at any temperature; (ii) stable iDTZ solutions made using the method and formulation work efficiently on cultured islets; (iii) the modified solution facilitates the staining process for automated islet counting apparatus, which usually requires more stable DTZ solution for imaging the islets; (iv) the method and formulation may be used to examine preserved and fixed islets, and as a quick and simple method to identify insulin-producing cells that derived from stem cells; (v) the proprietary stable iDTZ solution can be prepared by companies for selling to all islet transplant centers globally and lot to lot variability would not a problem; (vi) GMP grade and sterile DTZ solution may be prepared and used for FDA approved protocol of preparing islets for allo- and auto-transplantation; (vii) the stable DTZ solution can be used to quantify zinc in cells.

From the foregoing, it will be appreciated that specific embodiments of the invention have been described herein for purposes of illustration, but that various modifications may be made without deviating from the scope of the invention. Accordingly, the invention is not limited except as by the appended claims.

WORKING EXAMPLES

A new DTZ formulation (iDTZ for islet DTZ) and methods for its applications were evaluated as discussed in the working examples below. The working examples shown that improved solubility and optimized staining features and enhanced reproducibility of results, permitting automated analysis of human islet quality.

Example 1: New Islet DTZ (iDTZ) Formulation More Stable than Standard DTZ Solutions Materials and Methods Isolation of human pancreatic islets. Human islets were isolated from cadaveric donor pancreata procured from a local organ procurement organization following a standard operational procedure as described (29). The use of human islets was approved by the Institutional Review Board of City of Hope. All islets were cultured for 24-48 hours at 37° C., 5% $CO_2$ prior to staining with iDTZ or standard DTZ.

Preparation of DTZ. Standard DTZ solutions were prepared by dissolving 80 mg of Dithizone (Sigma, Cat #D5130-50G) in 10 mL of DMSO (Fisher Chemical, D128-

1), vortexed for 30 seconds, and then left at room temperature (22° C.) for 10 minutes. Using a 0.2 μm filter unit, 40 mL of DPBS (Ca2+ and Mg2+ free) was then added to the solution. To remove any visible particle precipitate, the final DTZ solution was passed numerous times through a 0.22 μm filter.

Preparation of iDTZ. To make 1 L of a stabilized iDTZ solution, Solution A and Solution B were made as follows:

Solution A. To make Solution A, 1.6 g Dithizone (Sigma cat #D5130) was added to 200 mL DMSO (Fisher cat #D128) and stirred to dissolve. Then, 120 mL methanol (Fisher cat #UHPLC-MS) was added. Stirring of the solution continued to increase the solubility of the DTZ. Next, approximately 8 mL of a 1 M Ammonium Hydroxide solution (Sigma, cat #338818) was added to the solution. Stirring was continued to completely dissolve without any particles. Stirring may take place under alkaline conditions, as the pH of Solution A could be 10.12.

Solution B. To make Solution B, a mixture of salts was combined with 16.8 ml of 1M HEPES buffer solution, then deionized and double distilled water was added up to 672 mL. The mixture of salts used are shown below in Table 4.

TABLE 4

| Solute | Source | Amount |
|---|---|---|
| Sodium chloride (NaCl) | Sigma cat # S1679 | 2.016 g |
| Sodium D-gluconate (D-Nagluconate) | Sigma cat# S2054 | 2.016 g |
| Sodium acetate trihydrate (NaAc•3H2O) | Sigma cat# S1429 | 2.7552 g |
| Potassium chloride (KCl) | Sigma cat# P1597 | 0.2016 g |
| Calcium chloride dihydrate (CaCl$_2$•2H2O) | Sigma cat# C8106 | 0.2 g |
| Magnesium chloride hexahydrate (MgCl$_2$•6H2O) | Sigma cat# M7304 | 0.164 g |

The solution was then adjusted to 7.2 pH.

Final working solution. The final ingredients with all ingredients were calculated for a total of 1 L solution. To make the final working solution, Solution B was slowly added to Solution A with continuous stirring. No particles or precipitation should form. The pH should be approximately 7.2. While iDTZ solution does not require filtration step as the solution should be clear, the final working solution may optionally be filtered using a 0.1-0.2 μm filter.

The final working solution is packaged in 100 mL bottles (or other desired size), an a certificate of analysis is issued for the final product. The expiration date of the final product is one moth from the date from the manufacturing.

Evaluation of standard DTZ and iDTZ solution stability. To compare the stability of both solutions in response to variations in temperature and time, solutions of standard DTZ and iDTZ were exposed to a range of temperatures: −80° C., −20° C., 4° C., 22° C., and 37° C. Visual analysis of solutions at each temperature was then undertaken at day 0, 7 and 30. Pictures were taken for each condition.

Discussion

Figure 1:
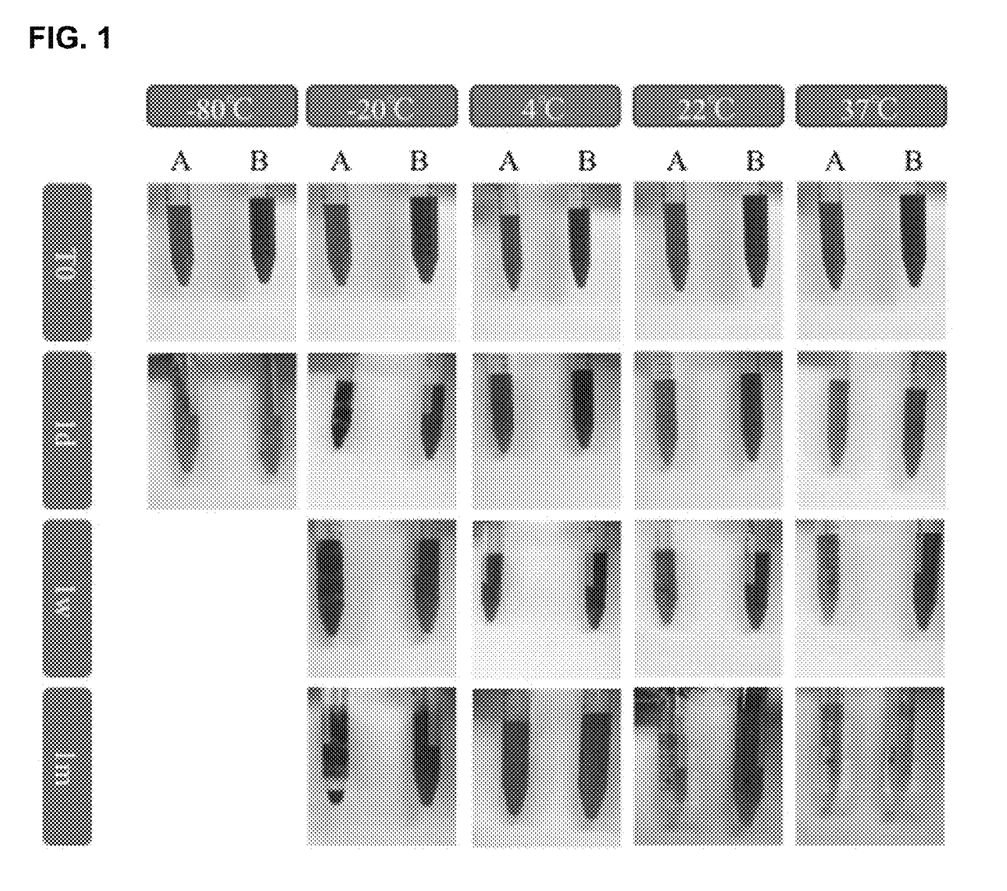
FIG. 1 shows that solutions of iDTZ show improved stability under various temperatures and lengths of time. Solutions were prepared as described using standard DTZ (A) and iDTZ (B) and exposed to a range of temperatures and storage intervals (−80° C., −20° C., 4° C., and 22° C. and 1, 7, and 30 days respectively).

At present, DTZ solutions require daily preparation as the existing formulation is partially soluble and precipitates rapidly. This is a major factor in the lack of reproducibility in characterizing islet β-cells (9) as well as other cell types such as yeast (10). In contrast to existing DTZ formulations, iDTZ was found to stable and highly soluble in solution. Solutions of iDTZ tolerated storage at −20 to 22° C. with no change in solution color or precipitation for up to one month post-preparation (FIG. 1). Further, solutions of iDTZ kept at 37° C. were stable while standard formulation DTZ solutions degraded within one week of preparation (FIG. 1). Thus, iDTZ solution possess physical and chemical stability and functionality within a temperature range expected in normal usage and handling.

Example 2: iDTZ Solution Staining is More Consistent and Efficient than Standard DTZ Solutions Materials and Methods Human pancreatic islets were isolated and DTZ/iDTZ solutions were prepared in accordance with the procedures discussed above in Example 1. Additional materials and methods are as follows.

Assessment of cell staining by standard DTZ and iDTZ solutions. To evaluate the staining efficacy, solutions were prepared fresh and used for staining the isolated islets. Islet morphology was observed and imaged using an automated islet cell counter (ICC) (Biorep Technologies, Miami, USA). Briefly, 100 μL of islet sample were pipetted (Drummond pipette, Fisher Scientific, USA) into an ICC provided dish (9). A 250 μL aliquot of standard DTZ or iDTZ solution was added and the dish agitated gently prior to placement on the imaging stage with the temperature at 22° C. Data was acquired at time zero (T0), 1 hr (T1), 2 hrs (T2) and 24 hrs (T24).

Assessment of islet staining with stored iDTZ solution. Human islets were stained with iDTZ solution that was stored for 6 months at −20° C. prior to use. In control experiments, freshly made iDTZ solution was used to stain islets from same cell preparation.

Discussion

Zinc is an important element present within insulin granules of the β-cells and has been shown to be involved in many diseases such as diabetes, cancer, neurodegeneration and wound healing (11). Zinc has been found to inhibit apoptosis in cells and currently serum- and animal tissue-free culture media contains zinc as a supplement to improve cells survival and function. Islets contain zinc ions ($Zn^{2+}$) and the zinc transporter channels ZnT and ZIP[12] are especially abundant in β-cells (13). Zinc ions are essential element in maintaining the structure and integrity of insulin molecules within β-cells and are secreted with insulin (14-16).

DTZ is relatively insoluble in water but solubilizes partially in ethanol, chloroform and DMSO. DTZ also readily complexes with transition metals and especially zinc, and can identify zinc-replete cells such islets within the pancreas (17) distinguishing islets from exocrine and ductal cells (18). For these reasons, DTZ staining is a standard technique for determining the number of islets in pancreatic digest and for assessing islet quality (18). Traditionally, this process involves manual assessment of DTZ-stained islets and thus is inherently variable. Automated methods for the quantification of stained islets have been reported (9, 19-21) with mixed results that were likely due, in part, to limitations in standard DTZ solution.

Figure 2A:
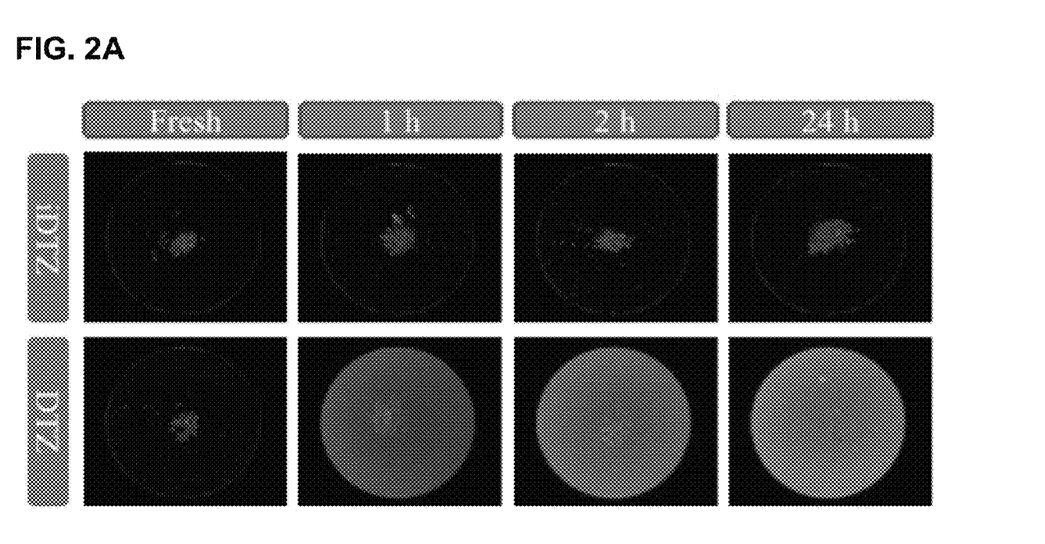
FIG. 2A shows human islets stained with iDTZ or standard DTZ solution visualized at the indicate time points.

To test this, standard DTZ was compared to iDTZ solution under varied conditions and parameters (9). Interestingly, over 24 hours islets stained with iDTZ displayed normal morphology and minimal increases in background staining. In contrast, islets stained with standard DTZ displayed intense background staining preventing automated quantification (FIG. 2a). In this regard, iDTZ solution is distinct in supporting islet quality validation over an extended period of time, an important factor in qualifying islets for clinical transplantation.

Figure 2B:
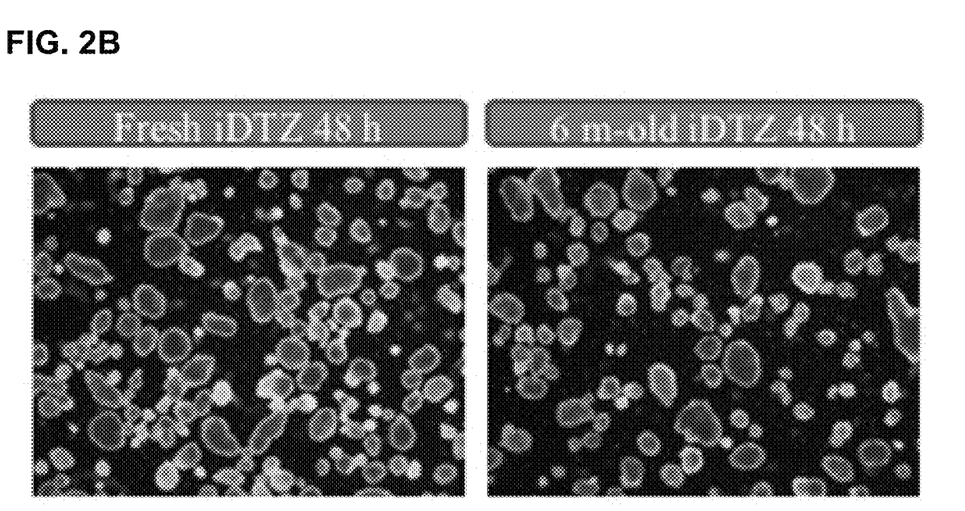
FIG. 2B shows human islets stained with fresh iDTZ solution and islets stained with iDTZ solution stored for 6 months at −20° C., both 48 hours post-staining.
Figure 2C:
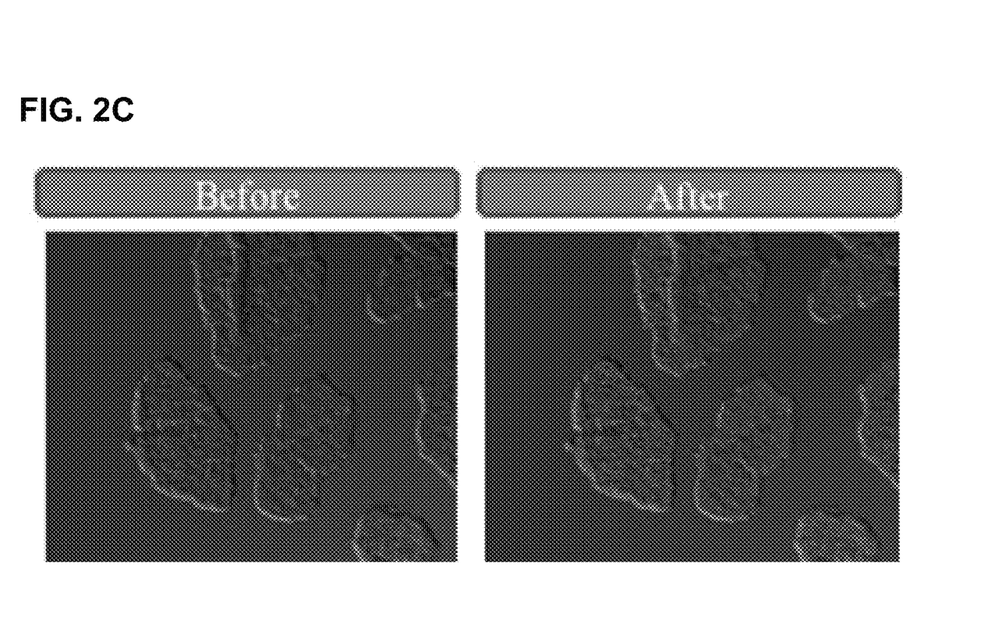
FIG. 2C shows human islet cryo-sections were stained with iDTZ solution. Representative pictures from three experiments are shown. All pictures were obtained using an Olympus microscope.

Solutions of iDTZ 6 months from preparation were found to provide islet-specific staining on par with freshly made solutions, an effect that persisted for 48 hours (FIG. 2b). These findings indicate that iDTZ staining creates a stable color signal that will allow for greater sharing of stained biomaterial without signal degradation. It was also found that iDTZ staining effective in demarcating islets in cryo-sections (FIG. 2c).

Both pancreas and prostate are known to have the abundant concentration of zinc compared to other organs (22). It has been suggested that Dithizone may not be sensitive to detect zinc in the tissues. However, it was found that solutions of iDTZ were sufficient for localizing islet-based zinc in pancreatic cryo-sections (FIG. 2c).

This reagent could be used as a simple, rapid means for detection of zinc in normal and cancer cells. In fact, prior studies noted zinc in normal prostates but this was diminished in cancerous organs (23). The process of isolating islets from cadaveric pancreata is complex, expensive and lengthy. Thus, using iDTZ solution to stain pancreatic biopsy cryo-sections prior to proceeding with islet isolation could be advantageous, especially when contemplating islet isolation from pancreata donated from individuals with high HbA1c, chronic diabetes and extensive insulin usage (24).

Example 3: iDTZ Solution can be Used to Detect Insulin Producing β-Cells at Different Stages of Development Materials and Methods Human pancreatic islets were isolated and DTZ/iDTZ solutions were prepared in accordance with the procedures discussed above in Example 1. Additional materials and methods are as follows.

Assessment of zinc and insulin status in differentiated stage 7 human embryonic stem cells. Human embryonic stem cells were differentiated following a previously published method (26). Briefly, human ES cell line H1 cells (WiCell Research Institute, Inc. Madison, Wis., USA) were cultured at 37° C., 5% $CO_2$ on Matrigel-coated plates (BD BioScience, cat #354671) in mTeSR™1 Complete Kit medium (StemCell Technologies, Vancouver, Canada, Catalog #85850) that was changed daily until cells were confluent. Cultured H1 cells were dissociated into single cells by incubation with Accutase (STEMCELL Technologies, Vancouver, Ca. cat #07920) for 5-10 minutes at 37° C. Single cells were counted and $5.5 \times 10^6$ in 5.5 mL mTeSR medium supplemented with 10 μM Y27632 (Stemgent, 04-0012-H-10) were seeded into 6-well low-attachment plates (Costar, #3471), placed on an orbital shaker (New Brunswick Innova 2000, #M1190-0000) set to 100 rpm to promote cluster formation and then cultured at 37° C., 5% $CO_2$. Forty-eight hours later the culture medium was changed into differentiation medium. Staged differentiation was conducted by the controlled addition of specific small molecules as described (26). At each stage, representative clusters were transferred into a new 6-well culture dishes and washed 3 times with 3 mL of COHSII (Gemini, Sacramento, Calif., Cat #900-7500) prior to staining with iDTZ. After 3 minutes, the cells were washed 3 times with 3 mL of COHSII again and resuspended with COHSII. Cell clusters were examined using a ckx31 Olympus microscope and pictures were acquired using a camera. The iDTZ solution employed was a single batch stored at −20° C. until use. Human islets stained with iDTZ were used as control.

Discussion

Figure 3A:
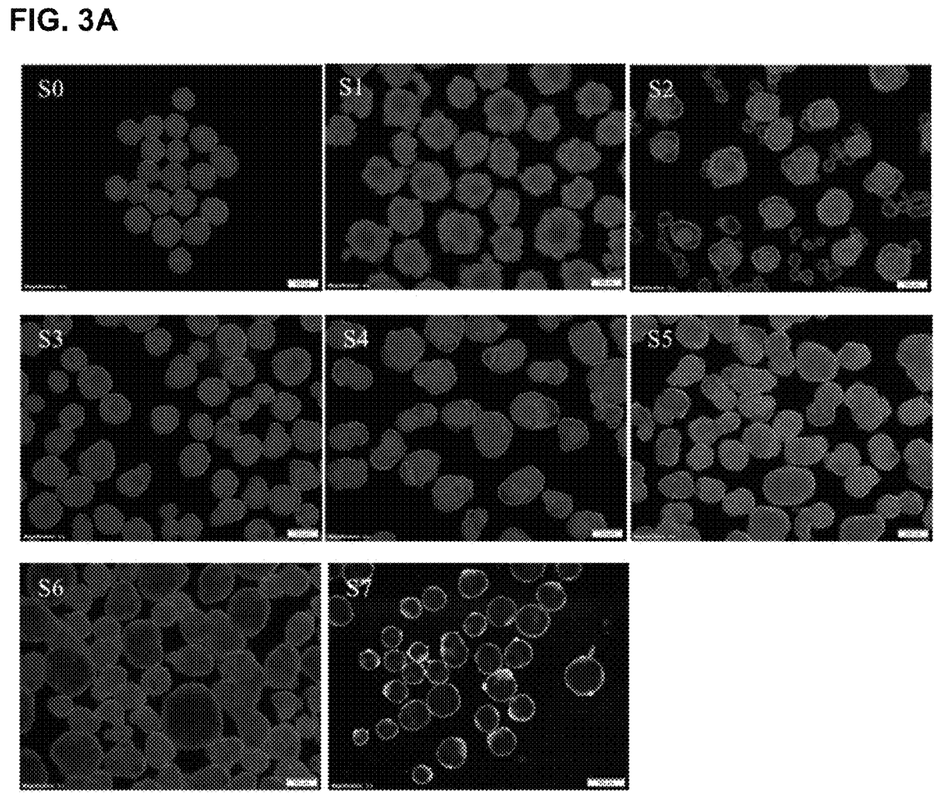
FIG. 3A shows that stage 6 and 7 cell clusters were stained positively as compared to other stages (1-5), which were negative for iDTZ.
Figure 3B:
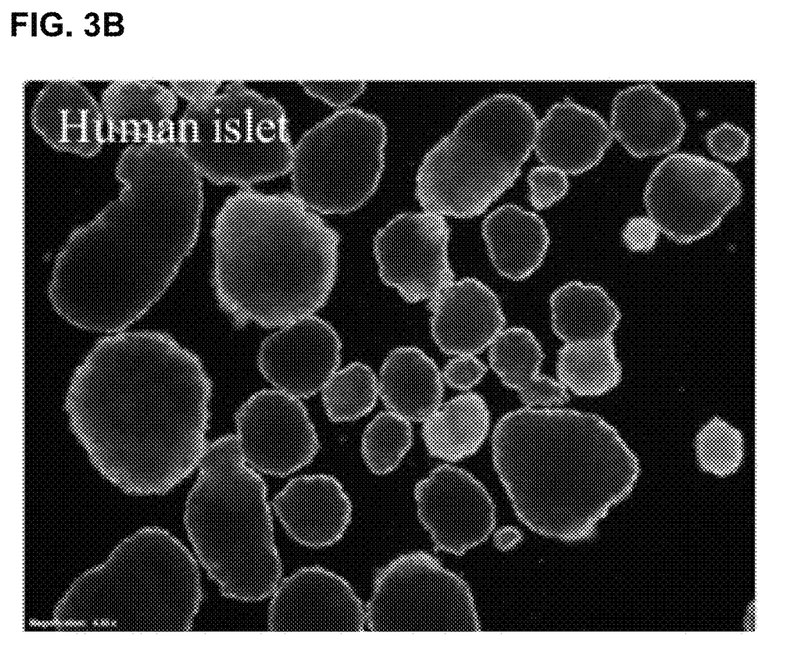
FIG. 3B shows human islets stained with iDTZ.
Figure 3C:
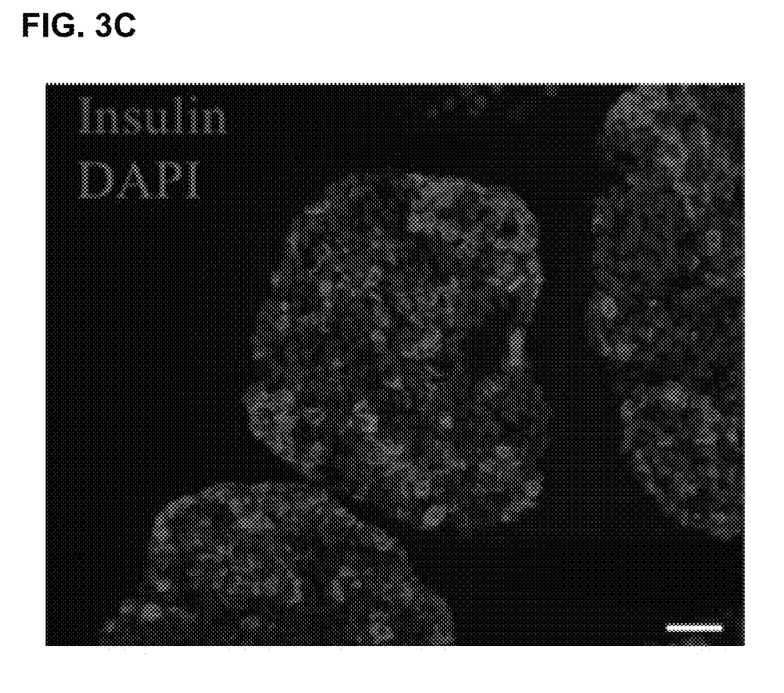
FIG. 3C shows immunofluorescent staining of stage 7 differentiated human embryonic stem cells showing insulin (Red), and DAPI staining in the nucleus (blue). The scale bar represents 50 μm.

The application of standard DTZ solutions beyond staining of mature islets is very limited. In one report, standard DTZ was used to stain stem cell-derived insulin-producing cells (25), suggesting that stem cell-derived islet-like cells or induced pluripotent cells, on differentiation, may display increased levels of zinc and insulin. To test this, the human embryonic cell line H1 was used (26). Cells were cultured under appropriate conditions for differentiation into insulin-producing cells using an established 7-stage protocol to complete differentiation (26). Clusters of cells were collected at every differentiation stage and stained with iDTZ. At stage 7, cells displayed a classic islet phenotype and, on iDTZ staining, were positive for intra-cellular zinc (FIG. 3a, b), concurrent with the presence of immuno-reactive insulin (FIG. 3c), a finding previously noted in stage 7 cells (26). Interestingly, it was found that approximately 10% of stage 6 cells retained iDTZ indicating that a portion of such cells are immature insulin-producing cells. Stage 7 clusters, despite staining with iDTZ, were noted to be de-granulated compared to mature adult human islets, indicating that stage 7 cell clusters would need further steps to attain full maturation and development (FIG. 3). Thus, iDTZ can be employed as a simple and robust method to identify fully mature insulin-producing β-cells prior to transplantation into recipients. Parenthetically, iDTZ could be used for rapid and simple agent to detect insulin producing cells transduced by several methods (27, 28).

Example 4: iDTZ Solution has High Sensitivity

Materials and Methods

Human pancreatic islets were isolated and DTZ/iDTZ solutions were prepared in accordance with the procedures discussed above in Example 1. Additional materials and methods are as follows.

Measurement of zinc concentration using iDTZ. $ZnCl_2$ (Sigma, CAS:7646-85-7) was dissolved using $MQH_2O$ to prepare a concentration of 200 μM. To test the sensitivity of the iDTZ readings, 50 μL of iDTZ [500 μM] was plated on a Black Flat Bottom 96-Well plate (Corning, Cat. No. 3631) with 50 μL of nine concentrations of $ZnCl_2$ (final concentration=100, 50, 25, 12.5, 6.25, 3.125, 1.56, 0.78, 0 μM). Control is 50 μL of 500 μM of iDTZ and 50 μL of water served as the blank. Each concentration was replicated twelve times. After 15 mins incubation at room temperature, the plate was read at 570 Absorbance using a Tecan reader infinite M200 (Tecan Group Ltd, Männedorf, Switzerland) and a linear standard curve was established.

Discussion

Figure 4:
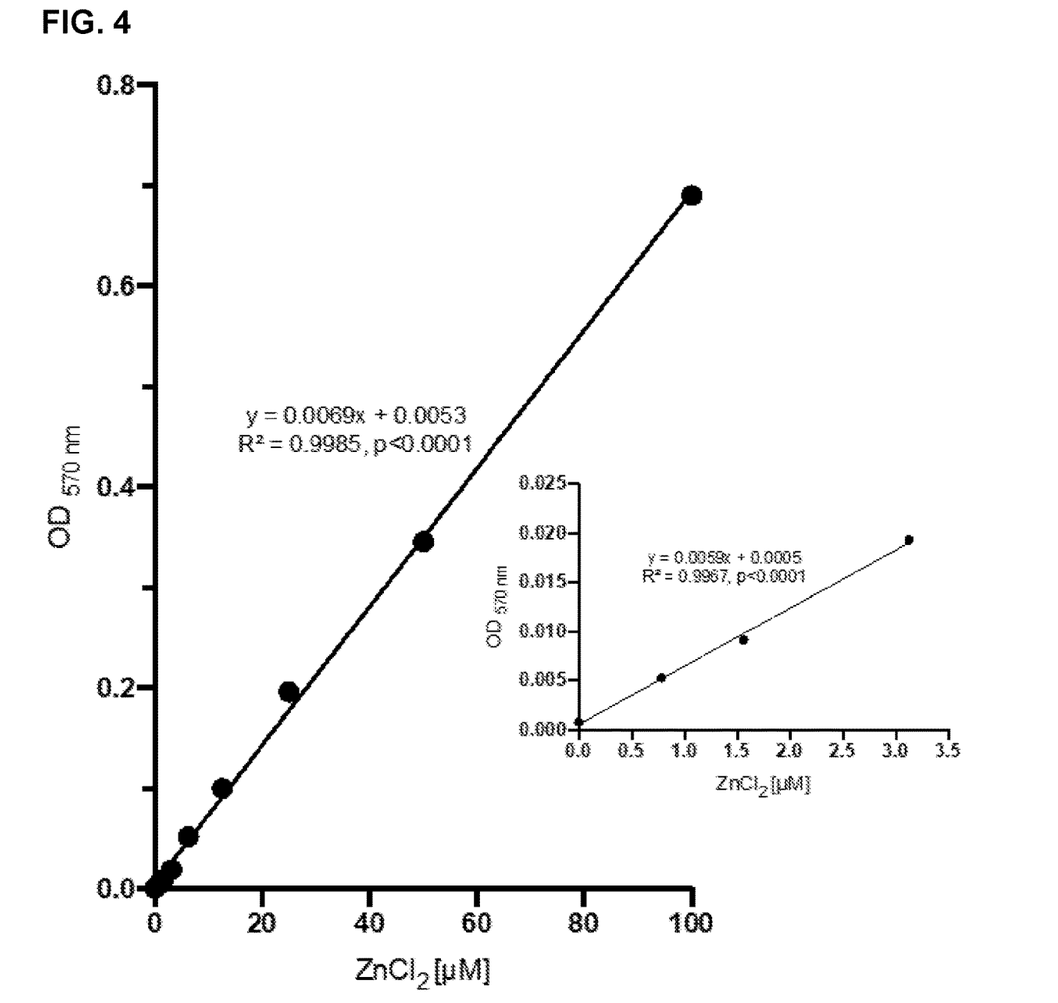
FIG. 4 shows that Zinc levels can be measured using iDTZ. There was a highly significant correlation between zinc concentration and the absorbance readings at 570 nm ($R^2=0.9985$, $p<0.0001$).

To further characterize the sensitivity of iDTZ to measure zinc levels a standard curve was developed for measuring dye levels at 570 nm in samples containing known concentrations of zinc chloride (FIG. 4). Extrapolating these results, it is likely that solutions of iDTZ could detect zinc in a range of tissue and fluid samples. Additionally, solutions of iDTZ may find application in detecting other metals such as lead, mercury, and cadmium. Currently characterization of zinc in liquids is done using a double beam flame absorption spectrophotometer or commercially available kits. However, these methods are complex and expensive. The sensitivity of the newly developed and stabilized iDTZ would of great advantage and can be performed in microplate and plate readers available in most laboratories.

REFERENCES

The references listed below, and all references cited in the specification above are hereby incorporated by reference in their entirety, as if fully set forth herein.

1. Zhou, Q. & Melton, D. A. Pancreas regeneration. Nature 557, 351-358 (2018).
2. Bakhti, M., Bottcher, A. & Lickert, H. Modelling the endocrine pancreas in health and disease. Nat. Rev. Endocrinol. (2018).
3. Bader, E. et al. Identification of proliferative and mature beta-cells in the islets of
Langerhans. Nature 535, 430-434 (2016).
4. Ellis, C., Ramzy, A. & Kieffer, T. J. Regenerative medicine and cell-based approaches to restore pancreatic function. Nat Rev Gastroenterol Hepatol 14, 612-628 (2017).
5. Kracht, M. J. et al. Autoimmunity against a defective ribosomal insulin gene product in type 1 diabetes. Nat. Med. 23, 501-507 (2017).
6. Hering, B. J. et al. Phase 3 Trial of Transplantation of Human Islets in Type 1 Diabetes Complicated by Severe Hypoglycemia. Diabetes Care 39, 1230-1240 (2016).
Ricordi, C. et al. National Institutes of Health-Sponsored Clinical Islet Transplantation Consortium Phase 3 Trial: Manufacture of a Complex Cellular Product at Eight Processing Facilities. Diabetes 65, 3418-3428 (2016).
8. Clark, S. A., Borland, K. M., Sherman, S. D., Rusack, T. C. & Chick, W. L. Staining and in vitro toxicity of dithizone with canine, porcine, and bovine islets. Cell Transplant. 3, 299-306 (1994).
9. Buchwald, P. et al. Fully Automated Islet Cell Counter (ICC) for the Assessment of Islet Mass, Purity, and Size Distribution by Digital Image Analysis. Cell Transplant. (2016).
10. Yuan, D. S. Dithizone staining of intracellular zinc: an unexpected and versatile counterscreen for auxotrophic marker genes in *Saccharomyces cerevisiae*. PLoS One 6, e25830 (2011).
11. Tian, X., Hussain, S., de Pace, C., Ruiz-Perez, L. & Battaglia, G. Zn(II) Complexes for Bioimaging and Correlated Applications. Chem Asian J (2019).
12. Jindal, R. M., Taylor, R. P., Gray, D. W., Esmeraldo, R. & Morris, P. J. A new method for quantification of islets by measurement of zinc content. Diabetes 41, 1056-1062 (1992).
13. Qian, W. J., Gee, K. R. & Kennedy, R. T. Imaging of Zn2+ release from pancreatic beta-cells at the level of single exocytotic events. Anal. Chem. 75, 3468-3475 (2003).
14. Li, D. et al. Imaging dynamic insulin release using a fluorescent zinc indicator for monitoring induced exocytotic release (ZIMIR). Proc. Natl. Acad. Sci. U.S.A 108, 21063-21068 (2011).
15. O'Halloran, T. V., Kebede, M., Philips, S. J. & Attie, A. D. Zinc, insulin, and the liver: a menage a trois. J. Clin. Invest. 123, 4136-4139 (2013).
16. Easley, C. J., Rocheleau, J. V., Head, W. S. & Piston, D. W. Quantitative measurement of zinc secretion from pancreatic islets with high temporal resolution using droplet-based microfluidics. Anal. Chem. 81, 9086-9095 (2009).
17. Mc, N. W., Jr. Zinc-dithizone reaction of pancreatic islets. J. Histochem. Cytochem. 2, 185-194 (1954).
18. Latif, Z. A., Noel, J. & Alejandro, R. A simple method of staining fresh and cultured islets. Transplantation 45, 827-830 (1988).
19. Friberg, A. S. et al. Quantification of the islet product: presentation of a standardized current good manufacturing practices compliant system with minimal variability. Transplantation 91, 677-683 (2011).
20. Kissler, H. J. et al. Validation of methodologies for quantifying isolated human islets: an Islet Cell Resources study. Clin. Transplant. 24, 236-242 (2010).
21. Wang, L. J. et al. Application of Digital Image Analysis to Determine Pancreatic Islet Mass and Purity in Clinical Islet Isolation and Transplantation. Cell Transplant. 24, 1195-1204 (2015).
22. Temiz, M. Z. et al. The use of serum zinc to prostate-specific antigen ratio as a biomarker in the prediction of prostate biopsy outcomes. Biomark. Med. (2019).
23. Christudoss, P., Selvakumar, R., Fleming, J. J. & Gopalakrishnan, G. Zinc status of patients with benign prostatic hyperplasia and prostate carcinoma. Indian J. Urol. 27, 14-18 (2011).
24. Qi, M. et al. Human Pancreatic Islets Isolated From Donors With Elevated HbA1c Levels: Islet Yield and Graft Efficacy. Cell Transplant. 24, 1879-1886 (2015).
25. Shiroi, A. et al. Identification of insulin-producing cells derived from embryonic stem cells by zinc-chelating dithizone. Stem Cells 20, 284-292 (2002).
26. Rezania, A. et al. Reversal of diabetes with insulin-producing cells derived in vitro from human pluripotent stem cells. Nat. Biotechnol. 32, 1121-1133 (2014).
27. Nair, G. G. et al. Recapitulating endocrine cell clustering in culture promotes maturation of human stem-cell-derived beta cells. Nat. Cell Biol. 21, 263-274 (2019).
28. Furuyama, K. et al. Diabetes relief in mice by glucose-sensing insulin-secreting human alpha-cells. Nature (2019).
29. Khiatah, B. et al. Evaluation of collagenase gold plus BP protease in isolating islets from human pancreata. Islets, e1417716 (2018).

We claim:

1. A stable solution of dithizone (DTZ) comprising:
a plurality of solutes comprising DTZ, ammonium hydroxide, and a salt mixture,
the salt mixture comprising a Zinc absorbing agent, wherein the Zinc absorbing agent is sodium D-gluconate; and
a solvent comprising a mixture of DMSO, methanol, water, and a buffering agent.

2. The stable solution of claim 1, wherein the concentration of DTZ is approximately 1.6 g/L, or the molar concentration of ammonium hydroxide is 1M.

3. The stable solution of claim 1, wherein the salt mixture comprises Sodium chloride (NaCl), sodium D-gluconate (D-Nagluconate), sodium acetate trihydrate (NaAc3•$_2$ O), potassium chloride (KCl), calcium chloride dihydrate (CaCl$_2$•2H$_2$ O), and magnesium chloride hexahydrate (MgCl$_2$•6H$_2$O).

4. The stable solution of claim 3, wherein the concentration of NaCl is between approximately 2 to 2.1 g/L, the concentration of D-Nagluconate is between approximately 2 to 2.1 g/L, the concentration of KCl is between approximately 2 to 2.1 g/L, the concentration of NaAc3·H$_2$ O is between approximately 2.7 to 2.8 g/L, the concentration of CaCl$_2$•2H$_2$ O is between approximately 0.15-0.25 g/L, or the concentration of MgCl$_2$•6H$_2$O is between approximately 0.1 to 0.2 g/L.

5. The stable solution of claim 1, wherein the solvent is approximately 20% DMSO, or approximately 12% methanol.

6. The stable solution of claim 1, wherein the buffering agent is a 1M HEPES solution.

7. A stable dithizone (DTZ) formulation comprising:
a first solution comprising DTZ dissolved in DMSO, methanol, and a solution of ammonium hydroxide;

a second solution comprising a salt mixture dissolved in water and a buffer solution, the salt mixture comprising a Zinc absorbing agent, wherein the Zinc absorbing agent is sodium D-gluconate;

wherein the first and second solution are combined to form a final DTZ solution.

8. The stable solution of claim 7, wherein the concentration of DTZ in final DTZ solution is approximately 1.6 g/L, or the molar concentration of ammonium hydroxide in final DTZ solution is 1M.

9. The stable solution of claim 7, wherein the salt mixture comprises Sodium chloride (NaCl), sodium D-gluconate (D-Nagluconate), sodium acetate trihydrate (NaAc3·$H_2$O), potassium chloride (KCl), calcium chloride dihydrate ($CaCl_2$·$2H_2$O), and magnesium chloride hexahydrate ($MgCl_2$·$6H_2$O).

10. The stable solution of claim 9, wherein the concentration of NaCl in the final DTZ solution is between approximately 2 to 2.1 g/L, the concentration of D-Nagluconate in the final DTZ solution is between approximately 2 to 2.1 g/L, the concentration of KCl in the final DTZ solution is between approximately 2 to 2.1 g/L, the concentration of $CaCl_2$·$2H_2$O in the final DTZ solution is between approximately 2.7 to 2.8 g/L, the concentration of $CaCl_2$·$2H_2$O in the final DTZ solution is between approximately 0.15-0.25 g/L, or the concentration of $MgCl_2$·$6H_2$O in the final DTZ solution is between approximately 0.1 to 0.2 g/L.

11. The stable solution of claim 7, wherein DMSO comprises approximately 20% of the final DTZ solution volume, or methanol comprises approximately 12% of the final DTZ solution volume.

12. The stable solution of claim 7, wherein the buffering agent is a 1M HEPES solution.

13. A method for preparing the stable solution of dithizone (DTZ) of claim 1 or 7 comprising
preparing a first solution comprising the following steps:
dissolving a quantity of DTZ in DMSO,
adding a solution of methanol to the DTZ dissolved in DMSO;
adding a solution of ammonium hydroxide to the DTZ dissolved in DMSO and methanol; and
stirring the solution of DTZ under alkaline conditions until the DTZ solution does not contain particles;

preparing a second solution comprising the following steps:
combining a salt mixture with HEPES buffer solution, the salt mixture comprising a Zinc absorbing agent, wherein the Zinc absorbing agent is sodium D-gluconate;
adding deionized and double distilled water to the salt mixture and HEPES buffer;
adjusting the pH of the salt buffer solution to approximately 7.2; and
combining the second solution with the first solution to form the stable solution of DTZ.

14. The method of claim 13, wherein the quantity of DTZ is approximately 1.6 g, or the molar concentration of the solution of ammonium hydroxide in the stable solution of DTZ is approximately 1M.

15. The method of claim 13, wherein the salt mixture further comprises sodium chloride (NaCl), sodium acetate trihydrate (NaAc3·$H_2$O), potassium chloride (KCl), calcium chloride dihydrate ($CaCl_2$·$2H_2$O), and magnesium chloride hexahydrate ($MgCl_2$·$6H_2$O).

16. The method of claim 15, wherein the concentration of NaCl in the stable solution of DTZ is between approximately 2 to 2.1 g/L, the concentration of D-Nagluconate in the stable solution of DTZ is between approximately 2 to 2.1 g/L, the concentration of KCl in the stable solution of DTZ is between approximately 2 to 2.1 g/L, the concentration of NaAc3·$H_2$O in the stable solution of DTZ is between approximately 2.7 to 2.8 g/L, the concentration of $CaCl_2$·$2H_2$O in the stable solution of DTZ is between approximately 0.15-0.25 g/L, or the concentration of $MgCl_2$·$6H_2$O in the stable solution of DTZ is between approximately 0.1 to 0.2 g/L.

17. The method of claim 13, wherein DMSO comprises approximately 20% of the stable solution of DTZ volume, or methanol comprises approximately 12% of the stable solution of DTZ volume.

18. The method of claim 13, wherein the molar concentration of the HEPES buffer solution in the stable solution of DTZ is approximately 1M.

19. The method of claim 13, wherein the method does not require filtering the stable solution of DTZ.

* * * * *